(12) United States Patent
Nyholm et al.

(10) Patent No.: US 11,259,761 B2
(45) Date of Patent: Mar. 1, 2022

(54) COMPUTED TOMOGRAPHY AND POSITIONING OF A VOLUME TO BE IMAGED

(71) Applicant: PLANMECA OY, Helsinki (FI)

(72) Inventors: Kustaa Nyholm, Helsinki (FI); Lauri Seppala, Helsinki (FI); Tero Pihlajamaki, Helsinki (FI)

(*) Notice: Subject to any disclaimer, the term of this patent is extended or adjusted under 35 U.S.C. 154(b) by 0 days.

(21) Appl. No.: 16/494,492

(22) PCT Filed: Mar. 19, 2018

(86) PCT No.: PCT/FI2018/050198
§ 371 (c)(1),
(2) Date: Sep. 16, 2019

(87) PCT Pub. No.: WO2018/167375
PCT Pub. Date: Sep. 20, 2018

(65) Prior Publication Data
US 2020/0085387 A1 Mar. 19, 2020

(30) Foreign Application Priority Data
Mar. 17, 2017 (FI) .................................. 20175240

(51) Int. Cl.
*A61B 6/00* (2006.01)
*A61B 6/14* (2006.01)
*A61B 5/00* (2006.01)
*A61B 6/03* (2006.01)
*A61B 6/08* (2006.01)

(52) U.S. Cl.
CPC .............. *A61B 6/14* (2013.01); *A61B 5/4542* (2013.01); *A61B 6/032* (2013.01); *A61B 6/08* (2013.01); *A61B 6/461* (2013.01); *A61B 6/469* (2013.01); *A61B 6/4441* (2013.01)

(58) Field of Classification Search
None
See application file for complete search history.

(56) References Cited

U.S. PATENT DOCUMENTS

| 2011/0129058 A1* | 6/2011 | Ulrici ....................... A61B 6/14 378/4 |
| 2015/0078508 A1 | 3/2015 | Lee et al. |
| 2016/0166205 A1 | 6/2016 | Ernst et al. |
| 2016/0174930 A1 | 6/2016 | Braun et al. |
| 2019/0357861 A1* | 11/2019 | Varlet .................. A61B 5/1077 |

FOREIGN PATENT DOCUMENTS

| EP | 2130491 A1 | 9/2009 |
| WO | 2016156150 A1 | 10/2016 |

OTHER PUBLICATIONS

International Search Report for PCT Application PCT/FI2018/050198, dated Jun. 27, 2018, 5 pages.

* cited by examiner

*Primary Examiner* — Hoon K Song
(74) *Attorney, Agent, or Firm* — Fay Sharpe LLP

(57) ABSTRACT

The invention relates to positioning a volume to be imaged for computed tomography imaging. According to the invention, at least two optical cameras (22) are used for taking a photo or for live imaging an anatomy from different directions. A volume positioning indicator (42) is shown in connection with these images, the volume positioning indicator (42) indicating the location of the volume within the area imaged by the cameras (22) to get imaged by the computed tomography imaging apparatus (10).

17 Claims, 4 Drawing Sheets

COMPUTED TOMOGRAPHY AND POSITIONING OF A VOLUME TO BE IMAGED

FIELD OF INVENTION

The invention relates to positioning a volume to be imaged for computed tomography imaging or, to put it in other words, directing imaging to a desired volume in an anatomy. The invention particularly relates to the computed tomography imaging of the human or animal cranial area.

BACKGROUND OF INVENTION

Medical computed tomography imaging (CT imaging) is a form of X-ray imaging in which a volume to be imaged is irradiated from different, directions and, from the data thus acquired, a desired two- or three-dimensional image is reconstructed afterwards. When X-ray imaging a person, the imaging must be implemented by as small a radiation dose as possible to still enable diagnosis. Due to this, one e.g. tries to keep the size and shape of the volume to be imaged as small as possible. For example, it is typical for dental cone-beam computed tomography (CBCT) that it does not produce image information of an anatomy for reconstructing a cross section of volume of a width of a complete skull but for reconstructing only a small volume, such as one covering a portion of a dental arch. Wishing to image a certain partial volume but simultaneously trying not to image anything diagnostically inessential naturally causes a problem of positioning the anatomy being imaged to the imaging apparatus such that specifically the desired volume of the anatomy can be imaged.

It is known to use in positioning of the anatomy e.g. various positioning lights, such as laser lines. Directing such lights to a desired point in the anatomy always takes some time and, when the whole process is based mostly on 'educated guess' on the position of the volume desired to be imaged in relation to the external features of the anatomy, the positioning by even an experienced person can prove to having been inaccurate. In such cases, it is possible that the imaging must be renewed, which increases the patient's total radiation dose, is in general frustrating and requires extra time from both the patient and the personnel.

It is also known to facilitate directing of the imaging by taking a scout X-ray image of the anatomy by a small radiation dose, from which image, the position of the volume desired to get imaged can be identified. However, the quality of such scout images is typically quite poor and, on the other hand, even a small extra radiation dose does in any case always increase the radiation load.

BRIEF DESCRIPTION OF INVENTION

The object of the invention is to improve positioning of an anatomy, especially that of a human or animal head, for computed tomography imaging.

The invention as defined in the attached independent claims bases on a solution in which means for showing image information show at least a first and a second image of a human or animal head taken by at least two optical cameras from at least two directions, or a first and a second live image, and also a volume positioning indicator in connection with these images. The volume positioning indicator is arranged to point the position of the volume to be imaged in the 2D images in question, and it is also possible to arrange the volume positioning indicator to be used as a means by which the volume desired to be imaged from the anatomy can be pointed, selected or determined.

It is thus possible to apply the invention in practice e.g. such that the patient is positioned in the imaging area of the computed tomography imaging apparatus and at least a first and a second image of a human or animal head being imaged taken by at least two optical cameras from at least two different directions, or a first and a second live image are shown e.g. on a computer display or a display arranged into connection with the imaging apparatus. From these images, it is possible to point or select a volume desired to be imaged by means of the volume positioning indicator, after which, information on the position of the volume in question is transmitted as control data to a control system of the computed tomography imaging apparatus. In order for the control system to be able to know to which volume of the set of coordinates of the imaging apparatus the volume selected from the display corresponds, the solution also includes information on where the set of coordinates of the volume positioning indicator shown on the display is positioned in relation to the position of the X-ray image means of the computed tomography imaging apparatus. One solution for achieving this information is to arrange said at least two optical cameras as part of the structure of the computed tomography imaging apparatus such that their position with respect to the X-ray imaging means of the computed tomography imaging apparatus is known. Then, the position of the volume positioning indicator in images taken from different directions unambiguously determines the position of the volume being imaged in the set of coordinates of the imaging apparatus.

The solution according to the invention offers a novel kind of visual and easy-to-use possibility to direct the volume being imaged at a desired point in the patient's anatomy and in a way which does not increase radiation load. In directing imaging, it is possible to use several but also only one display which shows the above-mentioned at least two images. The display or displays can be positioned in a separate space protected from radiation and the directing can be performed from there, whereby there is no need to wait for the assisting person to exit from the imaging set for shelter from radiation after the directing.

Some preferable embodiments of the invention are presented in the attached dependent claims and described in more detail in the following.

BRIEF DESCRIPTION OF FIGURES

The invention is now described in more detail in reference to its preferable embodiments and the attached drawings, of which.

DETAILED DESCRIPTION OF INVENTION

Figure 1:
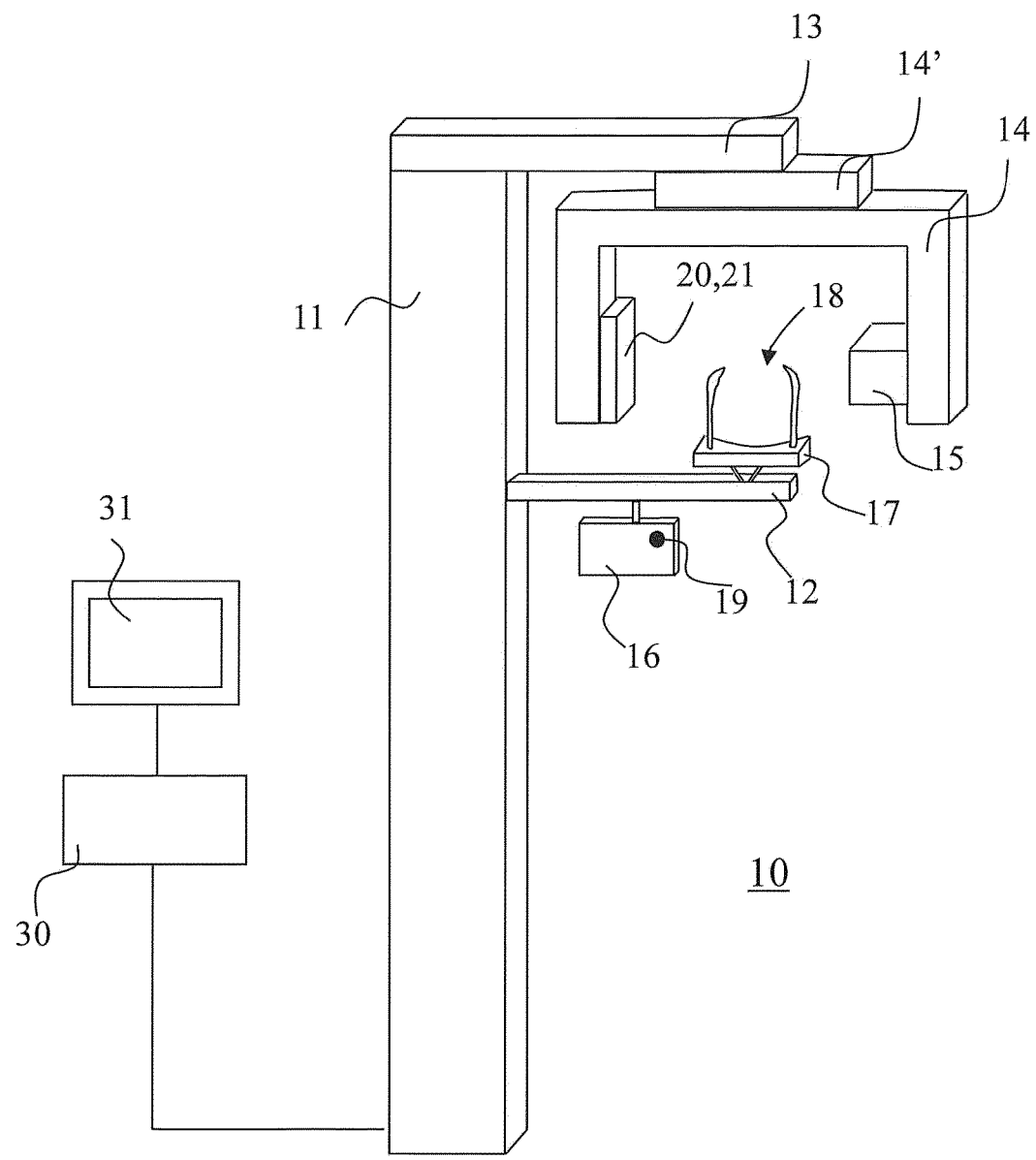
FIG. 1 shows a typical apparatus used in cone-beam computed tomography imaging.

FIG. 1 shows a basic structure of one apparatus suitable for use in computed tomography. The apparatus includes a vertical support construction 11 from which horizontally extends an arm 12 supporting patient support means and an arm part 13 which supports a structure supporting imaging means of the apparatus, an arm part 14. In the structure according to FIG. 1, the arm part 14 supporting the imaging means is arranged rotatable via a second rotatable arm part 14', which solution offers versatile possibilities for moving the imaging means. To the arm part 14 supporting the imaging means are arranged at a distance from each other an X-ray source 15 and a receiver of X-ray image information 21 which have been positioned to the apparatus with respect to a patient support means 17 such that to the apparatus is formed an imaging station 18 which is positioned between the X-ray source 15 and the receiver of X-ray image information 21 such that a beam produced by the X-ray radiation source 15 can be directed to pass via the imaging station 18 towards the receiver means of X-ray image information 21. The apparatus includes a control system in relation to which FIG. 1 shows a control panel 16 arranged to the support construction 11 and an operating mode selection means 19 pertaining in it. In the apparatus according to FIG. 1, the receiver means of X-ray image information 21 are arranged as part of a receiver module of image information 20, which is arranged into a functional connection with a computer 30 via e.g. a fixed or wireless connection, such as a cable, Bluetooth or wireless network. To the computer 30 are arranged means for processing image information and means for showing image information, which means include a display 31 for showing images generated by the computer 30.

Figure 2:
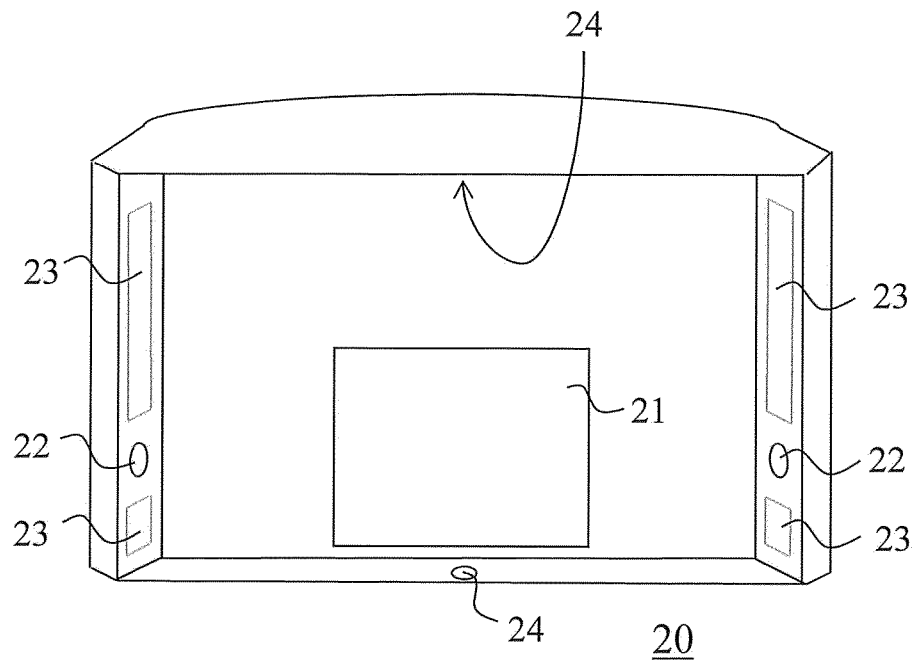
FIGS. 2 and 3 show a first and a second example of a receiver module of image information suitable for use in the apparatus according to FIG. 1.

FIG. 2 shows one receiver module of image information 20 applicable for use in the apparatus according to FIG. 1. The module includes two optical cameras 22 arranged horizontally on opposite sides of the receiver of X-ray image information 21 and directed at the imaging station 18. Furthermore, light sources 23 preferably producing white light arranged to light the imaging station 18 and two lasers 24 are arranged to the module 20. These lasers are positioned substantially in the middle of the module 20, in the substantial proximity of its upper and lower edges. The lasers 24 are arranged to emit and direct at the imaging station 18 a narrow vertical fan beam which casts a laser light pattern on the patient's face which can, while not directly relating to the present invention, be utilized when wishing to generate a surface model from the anatomy imaged by the cameras 22.

Figure 3:
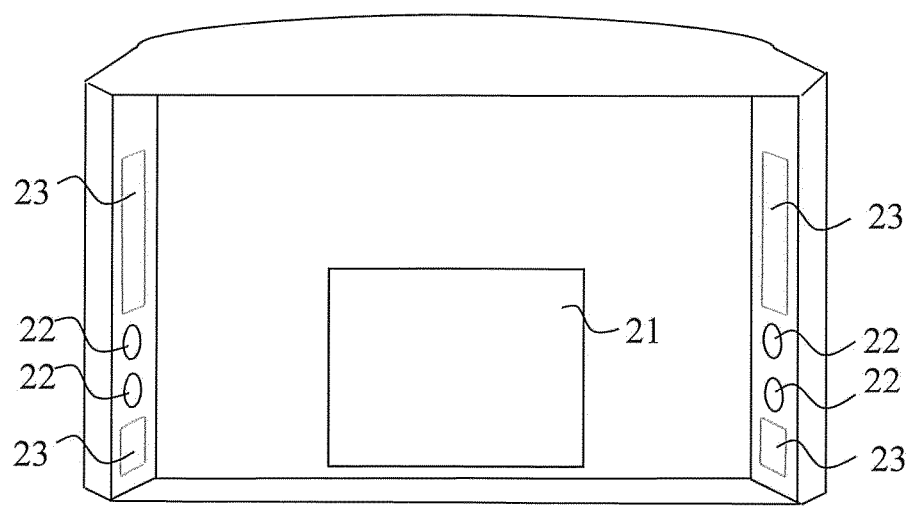

There can be more than two cameras 22. The cameras 22 can have been implemented to take individual photos but, in one preferred embodiment, they produce continuous live image from the imaging station 18. A module of the type described above can be implemented by accommodating only a part of the above-mentioned components in it. As an example of a different module, FIG. 3 shows a solution which includes no lasers 24 but which pertains cameras 22 on top of each other to form a camera pair on both edges of the module 20. Still, there can be cameras 22 in either direction and even in more than two. In one preferred embodiment of the invention, the module 20 nevertheless includes at least two optical cameras 22 at a horizontal distance from each other and the module 20 has been arranged to the computed tomography apparatus such that it is possible to take an image of a human or animal head from two different directions.

Figure 4:
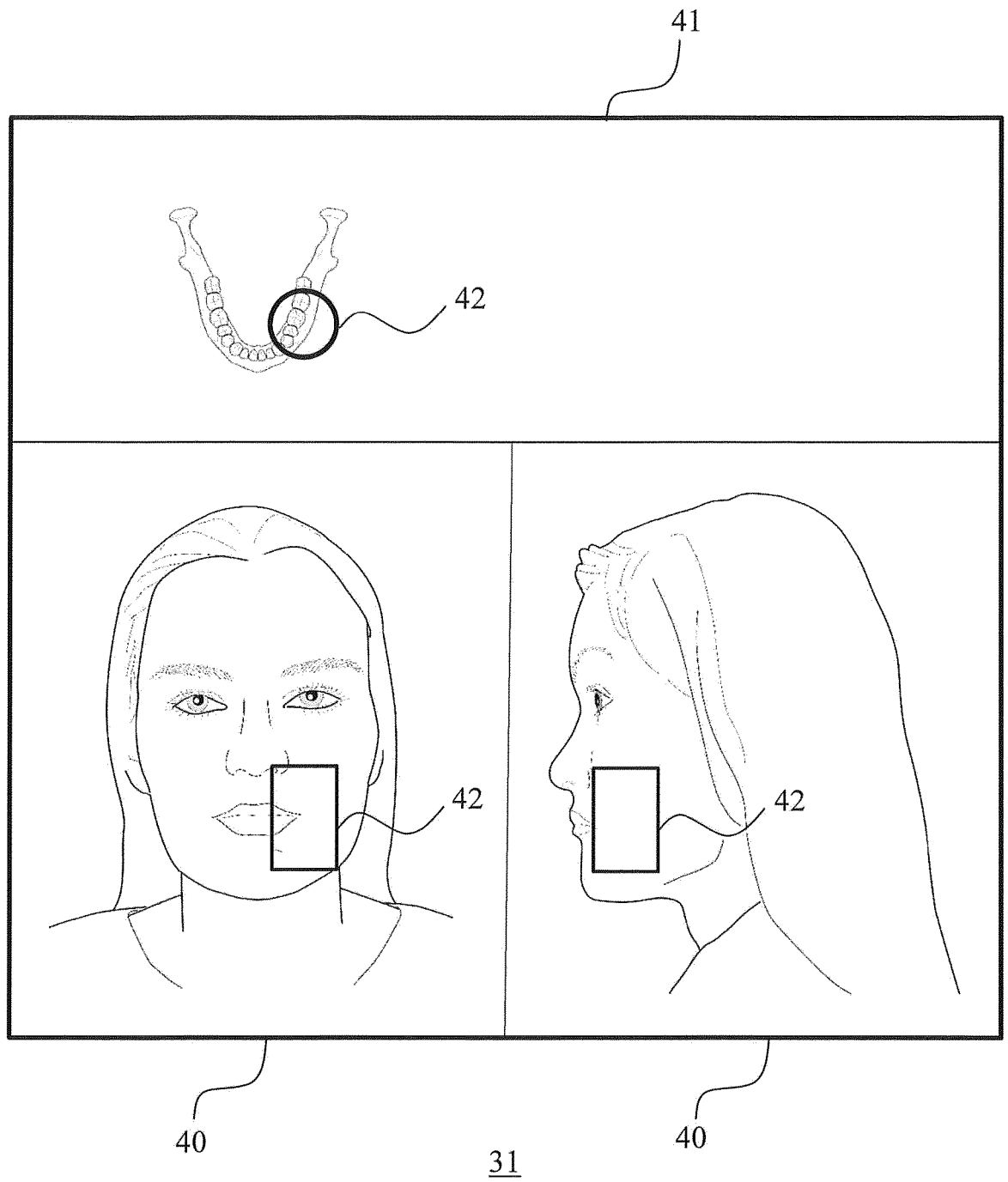
FIG. 4 shows a display which shows images of a human head taken by optical cameras from two directions, an image of a dental arch, and a volume positioning indicator in connection with each image.

FIG. 4 shows a display 31 which shows a first and a second image 40 of a human head taken by two optical cameras 22 from two directions positioned substantially on the same plane and a third image 41 showing the jawbone from a direction perpendicular with respect to these directions. In connection with each of these images is also shown a volume positioning indicator 42.

Even though the positioning of the anatomy can have been arranged to be implemented by positioning the patient to a desired point in the imaging station 18 of the apparatus according to the position of the volume positioning indicator 42 in the display with respect to the image to be taken from the patient, there is no need to move the patient at all in one preferable embodiment of the invention but the volume positioning indicators 42 can be arranged movable on the display and the apparatus to image particularly that volume within the operating range of the imaging apparatus the position of the volume positioning indicator 42 on the display 31 indicates.

In one embodiment of the invention, the display 31 shows the above-mentioned first and second photos 40, whereby the volume positioning indicator 42 is then arranged to be shown in these photos, or live images presenting the anatomy being imaged.

The volume positioning indicator 42 may be arranged movable to a desired point in each photo or live image 40 independently, whereby the position of the volume getting imaged is determined by the areas indicated in those images by means of the volume positioning indicator 42.

In one preferable embodiment of the invention, showing of the volume positioning indicator 42 in at least two photos or live image 40 has been implemented to be based on information of the shape of the jawbone 41 or the dental arch integrated in the system, in other words, the showing of the volume positioning indicator 42 in the 2D photos or live images 40 also includes depth information related to the anatomy desired to be imaged. Then, the position of the volume positioning indicator 42 in each image or live image 40 can always be made to correspond its position with respect to the jawbone. Hence, if the volume positioning indicator 42 is moved e.g. in an image taken from the side of the head from the area of the back teeth towards the area of the front teeth, it will move correspondingly in an image taken from the front, i.e. following the shape of the jawbone, towards the middle of the image.

Corresponding synchronization can also be implemented in an image showing the jawbone 41, in which the volume positioning indicator 42 can have been arranged to move substantially following the shape of the jawbone.

Thus, in one preferable embodiment of the invention, the display 31 shows all the images shown in FIG. 4 and, when the volume positioning indicator 42 is moved from one place to another in any of these images, it automatically moves in the other images to a position which corresponds the position of that volume which has been selected in some other image. And it is then also possible to implement such a function also such that the display 31 does not show an image of the dental arch 41 but the showing of the volume positioning indicator 42 in the first and the second image 40 is synchronized such that the position of the volume positioning indicator 42 always corresponds to some position on the dental arch.

It is also possible to indicate the three-dimensional position of the volume getting imaged by changing the size of the volume positioning indicator 42. E.g. in the example described above, the volume positioning indicator 42 would start to enlarge in an image of the anatomy taken from the front as it transfers from the area of the back teeth towards the area of the front teeth—and thus closer to the camera which has taken the above-mentioned image. Here, the size of the volume in the anatomy actually does not change but the size of the volume positioning indicator 42 on the display changes, when the patient stays in place and the volume positioning indicator 42 moves closer to the viewer—that is, closer to the camera taking the image.

The above-described synchronized operation may be implemented based on information stored in the system about the shape of the jawbone or the dental arch and an algorithm which always shows the volume positioning indicator 42 on the display 31 in some position of the stored shape. Preferably, information of at least two different jawbones is stored to the system to offer the user of the apparatus a possibility to select a default anatomy shape and/or size corresponding best the anatomy being imaged at each time. Naturally, it is also possible to use information on the shape of the particular anatomy being imaged, insofar as such information has been supplied for use to the system.

It should be emphasized once more that the operation in which the volume positioning indicator 42 is always positioned in the supposed jawbone area can be applied both in the context of an embodiment in which the display 31 only shows the images or live images of the anatomy taken from different directions and an embodiment which additionally shows an image of the jawbone.

In FIG. 4, the volume positioning indicator 42 is shown from different directions as a 2D image to correspond a volume to get imaged of a shape of a cylinder but it can be shown in some other shape as well. One preferable embodiment the solution shown in FIG. 4 particularly enables is to implement the display 31 as a touch screen and realize changing the position and dimensions of the volume positioning indicator 42 shown on the display 31 directly on that display. This solution enables a visual and easy-to-use way to determine the volume of the cranial area desired to get imaged. Naturally, the dimensions of the volume positioning indicator 42 can be arranged adjustable in some other way as well, for example, by determining them numerically from a user interface pertaining to the arrangement.

Figure 5:
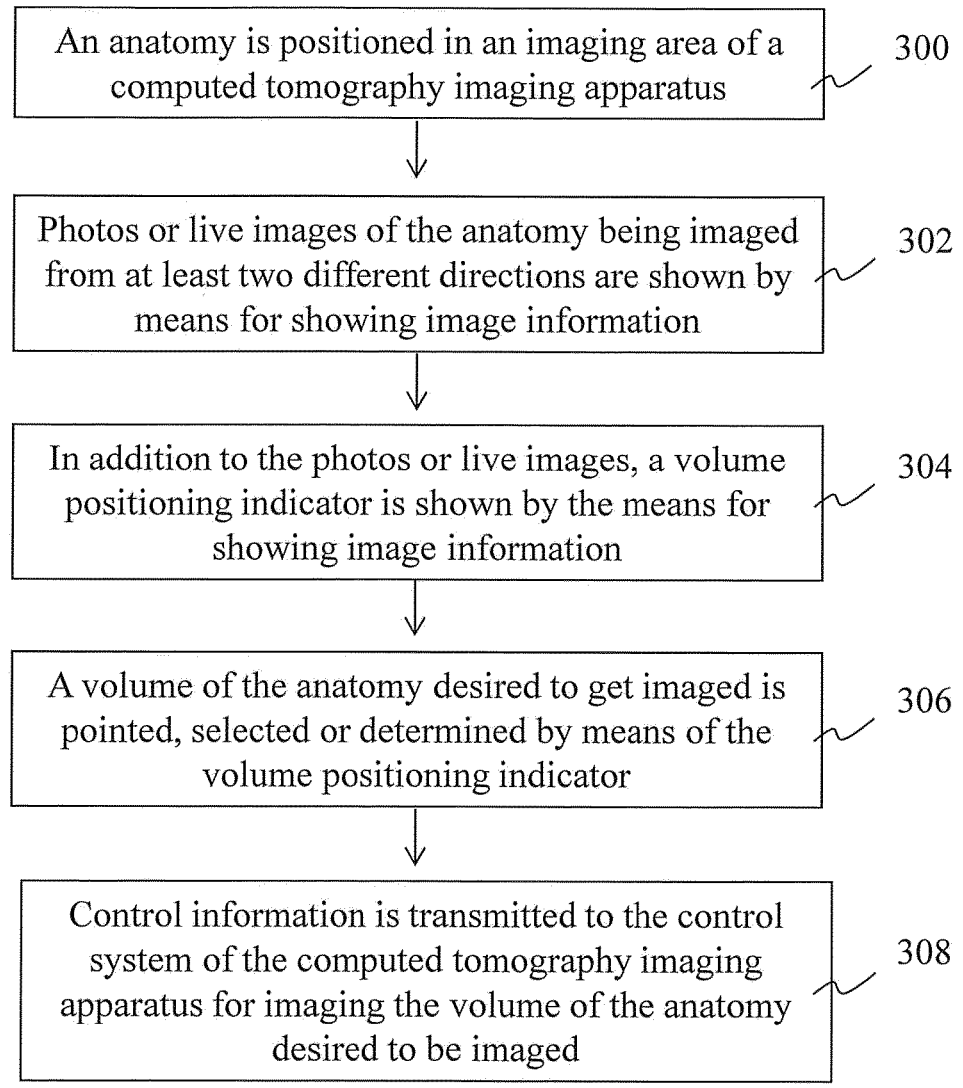
FIG. 5 shows one method according to the invention for positioning an anatomy for computed tomography imaging.

FIG. 5 presents a method for directing computed tomography imaging to a desired volume of an anatomy being imaged. The method can utilize e.g. an arrangement shown in FIG. 1, which comprises a computed tomography imaging apparatus including X-ray imaging means, a control system of the computed tomography imaging apparatus, and means for showing image information arranged into a functional connection with the computed tomography imaging apparatus. The computed tomography imaging apparatus can be e.g. a computed tomography apparatus (CT) or a cone-beam computed tomography imaging apparatus (CBCT). The means for showing image information can comprise e.g. a display 31, such as the display of a computer, a phone or a tablet. The display can be e.g. a conventional one or a touch screen.

In the method in step 300, an anatomy is positioned in an imaging area of the imaging apparatus, e.g. in the case of an apparatus shown in FIG. 1, to the patient support means 17 of the imaging station 18. The means for showing image information, such as the display 31, show in step 302 images 40 of the anatomy being imaged taken by at least two optical cameras 22 from at least two different directions and, as discussed above, possibly also a third image 41 showing the jawbone seen from a perpendicular direction with respect to these directions. In step 304, the means for showing image information 31 additionally shows the volume positioning indicator 42 which indicates the position of the volume to get imaged by the computed tomography imaging apparatus within the area imaged by said cameras 22. The volume positioning indicator 42 may be arranged to indicate also the dimension of the volume desired to be imaged. In step 306, the position of the volume desired to become imaged is pointed, selected or determined by means of the volume positioning indicator 42 and, in step 308, control information is transmitted to the control system of the computed tomography imaging apparatus for imaging that volume of the anatomy desired to be imaged.

It has been already stated above that the volume positioning indicator 42 can be arranged movable directly on the display 31 and, alternatively or additionally, the volume positioning indicator 42 can be arranged movable e.g. by means of a computer mouse and/or keyboard. It is possible to show the volume positioning indicator 42 on the display in a desired shape and size. In one preferred embodiment of the invention, as also having already been disclosed above, it is shown in the images or live images as a rectangle the height and width of which correspond to that cylinder-shaped volume the imaging apparatus has been arranged to image. And if applying the embodiment of the invention which also utilizes the third image showing the jawbone 41, it is then possible to show in that image a circle showing a volume of corresponding size, i.e. a circle having a diameter corresponding that of the cylinder-shaped volume the imaging apparatus has been arranged to image. If the imaging apparatus enables imaging different-sized volumes, the dimensions of the volume positioning indicator 42 may be arranged changeable in a corresponding way.

In one embodiment of the invention, the computed tomography apparatus is thus arranged to enable imaging of volumes of more than one size and the dimensions of the volume positioning indicator 42 shown on the display changeable within corresponding limits. Thereby, both position of the volume positioning indicator 42 and its size with respect to the images shown on the display can be changed, and information on the position and size of thus determined volume be arranged to be transmitted to the control system of the imaging apparatus.

To sum up, the method according to the invention can be described as a method which utilizes an arrangement comprising a computed tomography imaging apparatus including X-ray imaging means, a control system of the computed tomography imaging apparatus and a means for showing image information arranged into a functional connection with the computed tomography imaging apparatus and in which a human or animal head comprising a volume desired to get imaged is positioned in the imaging area of the computed tomography imaging apparatus. In the method, the human or animal head is imaged by at least two optical cameras from at least two different directions and at least a first and a second image produced by the cameras taken from the at least two different directions, or a first and a second live image produced by them are shown by the means for showing image information. Furthermore, in connection with these first and second images is shown a volume positioning indicator which indicates the position of the volume to get imaged by the computed tomography imaging apparatus within the area imaged by the cameras. By means of this volume positioning indicator, the position of the volume desired to be imaged by the computed tomography apparatus is then pointed, selected or determined by positioning the volume positioning indicator to a desired point in the images taken by the cameras.

In one embodiment of the method, the volume positioning indicator is arranged to get positioned in the second image always at a point with respect to a particular head-area anatomy which corresponds to its position in the first image.

According to one preferable embodiment, the first image is taken from the direction of the human or animal face and the second image substantially from the side of the head, both of these images substantially in the direction of a plane determined by the dental arch. The means for showing image information show in addition to thus taken images a third image indicating the jawbone or the dental arch, seen from a perpendicular direction with respect to the plane determined by said dental arch, which all images also show the volume positioning indicator, and the position of the volume positioning indicator is always shown in the first and the second image in a corresponding position in the imaging area as where it is located according to the third image.

The optical camera used in the method is preferably a camera producing live image and the first and the second image shown on the display are thus real-time image of a head positioned in the imaging area.

The pointing, selecting or determining the position of the volume desired to be imaged can comprise at least one of measures i) moving the anatomy in said imaging area, ii) moving the volume positioning indicator shown by means of said means for showing image information, iii) moving the X-ray imaging means, the dimensions of the volume positioning indicator can be changeable and in images taken by the cameras, the volume positioning indicator can be of a shape of a rectangle and in connection with an image showing the jawbone or the dental arch, correspondingly, a circle.

The cameras used in the method may be integrated to be a part of a camera arrangement of a computed tomography imaging apparatus and they can also be used for identifying the position of the patient in the imaging area during computed tomography imaging. Then, insofar as the position of the anatomy is noticed to change, the movement of the X-ray imaging means of the imaging apparatus can be controlled during imaging to compensate the change in the patient's position.

A computed tomography imaging apparatus according to the invention again can be described as comprising X-ray imaging means which includes an X-ray radiation source and a receiver means of image information, an imaging station, a control system, means arranged into a functional connection with the computed tomography imaging apparatus for processing image information and means for showing image information as well as at least two cameras positioned at a distance from each other and directed or being directable towards said imaging station. The control system of the apparatus includes means for showing images or live image produced by the cameras and also the volume positioning indicator in connection with these images, and means for pointing, selecting or determining the position of the volume desired to get imaged by means of the volume positioning indicator by positioning the volume positioning indicator to a desired point in the images.

The control system of the apparatus can comprise means for adjusting at least one of the following: position of the volume positioning indicator in the images; one or more dimensions of the volume positioning indicator; the position of the X-ray imaging means with respect to the imaging station.

The apparatus may be arranged to take a first image substantially from a direction of the human or animal face and a second image substantially from the side of the head, both of these images substantially in a direction of a plane determined by the dental arch. Furthermore, the means for showing image information may be arranged to show a third image indicating a jawbone or a dental arch, seen from a perpendicular direction with respect to the plane determined by said dental arch. The volume positioning indicator may be arranged to be shown in all of these images, and the position of the volume positioning indicator is arranged to be shown in said first and second image always at a point in the imaging station according to where it is located in said third image.

Various features of the invention may have been described above in part in a more general terms or as a part of an imaging process while it is clear that features of the invention the implementation of which relates to structures or functions of an imaging apparatus, such as functions implemented according to a configuration of a control system, pertain in the features of an imaging apparatus according to the invention.

It is obvious for those skilled in the art that when technology advances, the basic idea of the invention may be implemented in many different ways. The invention and its embodiments are thus not limited by the examples described above but they may vary within the scope of the patent claims.

The invention claimed is:

1. A method for positioning a volume to be imaged for computed tomography imaging, in which method, an arrangement is used which comprises a computed tomography imaging apparatus including an X-ray imaging device including an x-ray source and receiver, a control system of the computed tomography imaging apparatus and a display for showing image information arranged into a functional connection with the computed tomography imaging apparatus, in which method a human or animal head including a volume desired to get imaged is positioned in the imaging area of the computed tomography imaging apparatus, said human or animal head is imaged by at least two optical cameras from at least two different directions at least during a portion prior to activation of the x-ray source and at least a first and a second image from at least two different directions produced by said cameras are live stream images shown by said display of said head positioned in the imaging area, in connection with said first and second images, a volume positioning indicator is shown which indicates a position within the area imaged by said at least two cameras of the volume to get imaged by the computed tomography imaging apparatus, position of the volume desired to get imaged by said computed tomography apparatus is pointed, selected or determined using said volume positioning indicator by positioning the volume positioning indicator to a desired point in said first and second images, wherein when changing location of the volume positioning indicator in the first image such that the volume positioning indicator gets closer or further away from the optical camera generating the second image, a size of the volume positioning indicator in the second image as seen from the direction of the second camera is changed to be larger when the volume positioning indicator is moved closer to the second camera, and vice versa.

2. A method according to claim 1, wherein said volume positioning indicator shown in the at least two images has been arranged to get positioned in the second image always at a point with respect to a particular head-area anatomy which corresponds to its position in the first image.

3. A method according to claim 1, wherein said first image is taken substantially from the direction of the human or animal face and the second image substantially from the side of the head, both said first and second images from the direction of a plane determined by a dental arch, and by said display is shown, in addition to thus taken first and second image, a third image indicating a jawbone or a dental arch as seen from a perpendicular direction with respect to the plane determined by said dental arch and in all of which images, also the volume positioning indicator is shown, and the position of the volume positioning indicator is shown in said first and second image always at a point in the imaging area according to where it is located in said third image.

4. A method according to claim 1, wherein dimensions of said volume positioning indicator are changeable.

5. A method according to claim 1, wherein the pointing, selecting or determining of the position of said volume desired to be imaged comprises at least one of actions i) moving the anatomy in said imaging area, ii) moving the volume positioning indicator shown using the display, iii) moving the X-ray imaging device.

6. A method according to claim 1, wherein the volume positioning indicator shown in connection with said first and second image is a rectangle.

7. A method according to claim 1, wherein a third image indicating a jawbone or a dental arch as seen from a perpendicular direction with respect to the plane determined by said dental arch is shown and wherein the volume positioning indicator shown in connection with said third image is a circle.

8. A method according to claim 1, wherein said at least two optical cameras are part of a camera arrangement arranged in the computed tomography imaging apparatus.

9. A method according to claim 8, wherein said two optical cameras are used for identifying a position of a patient in the imaging area during computed tomography imaging and if the position is detected to change, the motion of said X-ray device is controlled during the imaging to compensate for the change in the position of the patient.

10. A method according to claim 1, wherein the imaging apparatus is arranged moveable to image the volume designated by the positioning indicator on the display.

11. A method according to claim 1, wherein the display shows multiple images and when the volume positioning indicator is moved from one place to another in one of these images it automatically moves in the other images to a position which corresponds to the position of that volume which has been selected in the one of the images.

12. The method of claim 1 wherein the volume desired to get imaged by said computer tomography apparatus is displayed in the live stream images and does not change in volume when the volume of the position indicator gets larger or smaller.

13. A computed tomography imaging apparatus which comprises an X-ray imaging device including an X-ray source and a receiver module, an imaging station, a control system, a means arranged in a functional connection with the computed tomography imaging apparatus for processing image information, and which apparatus additionally comprises
- at least two cameras located at a distance from each other, which are directed or directable at said imaging station, and configured to capture and forward a live image stream, and
- the control system of which apparatus comprises
- a display for showing a live image produced by said at least two optical cameras and in connection with these images, also a volume positioning indicator, and
- a user interface for pointing, selecting or determining a position of said volume positioning indicator to define a volume desired to get imaged in a desired point in said images, wherein the control system is configured such that when location of the volume positioning indicator is changed in a first image generated by a first optical camera getting closer or further away from a second optical camera generating a second image, a size of the volume positioning indicator in the second image is changed to be larger when the volume positioning indicator is moved closer in the direction of the second camera, and vice versa.

14. An apparatus according to claim 13, wherein said control system adjusts at least one of the following: position of said volume positioning indicator in said images; one or more dimensions of said volume positioning indicator; position of said X-ray imaging device with respect to the imaging station.

15. An apparatus according to claim 13, wherein said first image is arranged to be taken substantially from a direction of a human or animal face and the second image substantially from a side of the head, both said first and second images in direction of a plane determined by a dental arch, and said display are additionally arranged to show a third image indicating a jawbone or a dental arch, seen from a perpendicular direction with respect to the plane determined by said dental arch, in all of which images also the volume positioning indicator is arranged to be shown, and the position of the volume positioning indicator is arranged to be shown in said first and second image always at a point in the imaging station according to where it is located in said third image.

16. An apparatus according to claim 13, wherein the imaging apparatus is arranged moveable to image the volume designated by the positioning indicator on the display.

17. An apparatus according to claim 13, wherein the display shows multiple images and when the volume positioning indicator is moved from one place to another in one of these images it automatically moves in the other images to a position which corresponds to the position of that volume which has been selected in the one of the images.

* * * * *